United States Patent [19]

Kern et al.

[11] Patent Number: 5,330,903
[45] Date of Patent: Jul. 19, 1994

[54] METHOD FOR PRODUCING CAPSULAR POLYSACCHARIDES

[75] Inventors: Roger G. Kern, Pasadena; Gene R. Petersen, Pomona; Gil F. Richards, Duarte, all of Calif.

[73] Assignee: California Institute of Technology (JPL), Pasadena, Calif.

[21] Appl. No.: 799,419

[22] Filed: Nov. 27, 1991

[51] Int. Cl.$^5$ ............................................. C12P 19/04
[52] U.S. Cl. .................................................. 435/101
[58] Field of Search ........................................ 435/101

[56] References Cited

PUBLICATIONS

Tang et al., *Biological Abstracts*, vol. 90(8): #86261, Oct. 15, 1990.
Dutton et al., *Carbohydrate Research*, vol. 103 (1982), pp. 107–128.
"Industrial Applications of Some New Microbial Polysaccharides" By J. K. Baird, et al. 1983 pp. 778–783.
"Degradation of Bacterial Surface Carbohydrates By Virus–Associated Enzymes" By Hildegard Geyer, et al. 1983–pp. 637–653.
"Turbulent-Flow Properties of Polysaccharide Solutions" By J. W. Hoyt, 1968, pp. 207–215.
"Drag-Reduction Effectiveness of Polymer Solutions in the Turbulent-Flow Rheometer: A Catalog" By J. W. Hoyt, 1971, pp. 851–862.
"Drag Reduction in Polysaccharide Solutions" By: J. W. Hoyt, 1985, pp. 17–21.
"Yeasts Producing Exopolysaccharides with Drag-Reducing Activity" By G. R. Petersen, et al. 1990, pp. 255–259.
"Rheologically Interesting Polysaccharides From Yeasts" By Gene R. Petersen, et al. 1989 pp. 845–867.
"Structural Modification of Polysaccharides, A Biochemical-Genetic Approach" By: Roger G. Kern and Gene R. Petersen, Dec. 1991 pp. 73–78.
"Experiments in Molecular Genetics" By Jeffrey H. Miller, 1972, pp. 121–129.

*Primary Examiner*—Ronald W. Griffin
*Attorney, Agent, or Firm*—Graham & James

[57] ABSTRACT

Structurally altered capsular polysaccharides are produced by mutant bacteria. These polysaccharides are isolated by selecting a wild type bacterial strain and a phage producing degradative enzymes that have substrate specificity for the capsular polysaccharides produced by the wild type bacteria. Phage-resistant mutants producing capsular polysaccharides are selected and the structurally altered capsular polysaccharide is isolated therefrom.

9 Claims, No Drawings

METHOD FOR PRODUCING CAPSULAR POLYSACCHARIDES

The invention described herein was made in the performance of work under a NASA contract, and is subject to the provisions of Public Law 96-517 (35 U.S.C. § 202) in which the Contractor has elected to retain title.

This invention relates to novel and useful complex polysaccharides and methods for producing them. More particularly, this invention relates to structurally altered capsular polysaccharides produced by bacterial mutants.

BACKGROUND OF THE INVENTION

Complex polysaccharides have a variety of industrial applications. Generally these molecules alter the physical properties—including viscosity and rheology—of fluid media in which they are suspended. Accordingly, complex polysaccharides are used as thickeners in the food industry, for suspending waste fragments in drilling or cutting operations, and as water soluble lubricants. Baird et al., "Industrial Applications Of Some New Microbial Polysaccharides," *Biotechnology*, November 1983, pp. 778-83. For similar reasons, complex polysaccharides are also used to reduce turbulence of fluid flow in pipelines and other containers. J. W. Hoyt, Drag Reduction In Polysaccharide Solutions, *Trends In Biotechnology*, 3, 17-20 (1985). The physico-chemical basis for these effects is not understood, id. although correlations between drag reduction and the extensional viscosity of polysaccharides have been reported. G. R. Petersen et al., "Rheologically Interesting Polysaccharides From Yeasts", *Appl. Biochem. Biotech.*, 20/21, 845-67 (1989).

Because the basis for these useful properties of complex polysaccharides is not understood, the identification of useful complex polysaccharides requires screening of candidate polymers. Accordingly, it is desirable to develop methods for producing new candidate complex polysaccharides for evaluation.

SUMMARY OF THE INVENTION

Structurally altered capsular polysaccharides are produced by mutant bacteria. These polysaccharides are isolated by selecting a wild type bacterial strain and a phage producing degradative enzymes that have substrate specificity for the capsular polysaccharides produced by the wild type bacteria. Phage-resistant mutants producing capsular polysaccharides are selected and the structurally altered capsular polysaccharide is isolated therefrom.

DETAILED DESCRIPTION OF THE INVENTION

The cells of many bacterial species—specifically, gram positive bacteria—are surrounded by a glycocalyx also referred to as a capsular polysaccharide ("CPS") several hundred nanometers in thickness. The glycocalyx consists of a complex polysaccharide polymer that appears to be species specific. H. Geyer et al. "Degradation Of Bacterial Surface Carbohydrates By Virus-Associated Enzymes", *Pure And Applied Chemistry*, 55, pp. 637-53 (1983). Hence bacteria have proved to be an important source of complex polysaccharides. Baird et al. (1983). Bacteria are an especially desirable source of polysaccharides because of the purity and uniformity of the product.

Bacteriophage are viruses that infect bacteria. The viruses that infect bacteria encapsulated by a glycocalyx are specially adapted to penetrate the polysaccharide barrier. The tail fibers or spikes by which these viruses are seen to attach to bacteria contain enzymes—generally referred to as endoglycanases or endopolysaccharases—that degrade the glycocalyx. These enzymes exhibit a high degree of substrate specificity. Geyer et al, supra at pp. 38-39.

According to the present invention, a strain of encapsulated bacteria and the specific phage which infects it are employed. The selected bacteria are optionally exposed to a mutagenic agent. Examples of useful mutagenic agents include radiation and chemical mutagens, such as nitrosoguanidine. The mutagenized bacterial cells are grown to a desired density, and then screened for resistance to phage that specifically degrade the glycocalyx of the wild type strain. Surviving bacteria are likely to have a glycocalyx with altered chemical structure. The CPS of the selected bacterial strains is harvested with enzymes derived from phage. The isolated CPS is purified by known techniques and degraded to oligomer by further treatment with phage enzymes.

In one embodiment of the present invention, we employed a strain *Klebsiella pneumoniae* that produces a capsular polysaccharide known as K63, and a phage ("K63 phage") that specifically degrades the same polysaccharide. We obtained *Klebsiella pneumoniae* strain 5845/52 from the World Health Organization. This strain produces the K63 capsular protein. The K63 CPS is a straight chain heteropolymer of fucose, galacuronic acid and galactose, linked, in that order by α 1-3 glycosidic linkages. The K63 phage enzymatically hydrolyzes the α 1-3 linkage between the galactose and fucose monomers. Both the nature of the CPS polymer and the mode of action of the K63 phage enzyme are representative, and support the general applicability of our method.

We selected mutants for further study that were either spontaneously generated or were induced by exposure to the mutagenic agents nitrosoguanidine or ultraviolet radiation. J. H. Miller, *Experiments In Molecular Genetics* (1972). Following treatment to induce mutation, cells were grown on DIFCO Nutrient Broth, supplemented with 1% glucose, at 30° C., while rotated at 150 rpm. Cells were grown to early stationary phase ($OD^{590}$ of approximately 3.5). Calcium chloride (0.1 M) was added to stabilize the CPS matrix.

The fresh stationary phase culture, less than hours old, contained approximately $2.5 \times 10^9$ viable cells/ml. Phage 63 was added at a concentration sufficient to achieve a multiplicity of infection ("MOI") of between one and five. The culture was incubated at room temperature for about 10 minutes to permit phage to attach to the bacterial cells. The infected culture was then diluted 10 fold into fresh glucose supplemented nutrient broth and grown overnight to stationary phase.

Phage resistant mutants were isolated as single colonies on petri dishes after streaking with the overnight culture of infected bacteria. Resistant colonies that did not form plaques were selected. Phage resistance of the selected colonies was confirmed by administration of a drop of phage/enzyme concentrate. The zone of lysis produced by the diffusion of the phage/enzyme concentrate was dramatically reduced for those strains with phage resistance when compared with wild type bacteria.

Mutants whose phage resistance was due to altered CPS were selected from among those phage resistant mutants already identified. The phage resistant colonies were grown for 5 to 7 days so that mucoid (CPS producing) and non-mucoid mutant colonies could be distinguished. The colonies were retested for phage resistance as before. Mucoid mutants that remained phage resistant were assumed to have altered CPS. Non-mucoid phage resistant mutants were assumed to be resistant for other reasons, for example, lacking virus receptor sites. Approximately 90 % of the 5845/52 phage resistant mutants have altered CPS by this criterion.

In order to test the capacity of the altered CPS from mutant cells to affect rheological properties of aqueous media, we partially purified the CPS. The cultured mutant bacterial cells, like those produced by large-scale industrial fermentations, is resistant to high speed centrifugation. We succeeded in achieving substantial purification of the altered CPS using a concentrated extract of phage enzymes.

A concentrated mixture of CPS specific enzyme and phage fragments was prepared by preparing a phage lysate from stationary phase cultures, and concentrating the lysate 80 fold with an AMICON hollow fiber filter (HPI10), followed by dialysis to remove low molecular weight substances. The final concentration factor was 39. This material showed a 24-fold enhancement in enzymatic activity as determined by a reducing end sugar assay, as compared with crude phage lysate.

Phage/enzyme concentrate was added in small quantities—1 ml/liter—to cultures of mutant bacterial cells. This results in a rapid and dramatic reduction (>100 fold) in the viscosity of the culture media. Altered CPS was thereafter separated from the bacterial cells by low speed centrifugation at 20° C. Immediately after centrifugation, the supernatant was precipitated by the addition of 4 volumes of isopropanol at −20° C. We have also used cold ethanol in place of cold isopropanol. The resulting precipitate was rehydrated and extensively dialyzed against deionized water.

The CPS polymer obtained from wild-type K63 bacteria had and apparent molecular weight of $3.5 \times 10^6$ daltons. Digestion of this material with phage 63 enzyme reproducibly yielded a homogeneous mono-disperse polysaccharide with a molecular weight of $9.0 \times 10^5$ daltons.

We measured the drag reduction produced by undigested CPS harvested from wild type and mutant K63 bacteria using a turbulent flow rheometer fabricated according to the design of Hoyt [J. W. Hoyt, *Polymer Letts.*, 9, 851–62 (1971); J. W. Hoyt, "The solution Properties Of natural Polymers", *The Chemical Society Special Publication*, No. 23, (London) pp. 86–91 (1968)] modified by altering pipe diameter to operate at a fixed Reynolds number of 16,500. The drag reduction was calculated:

Drag Reduction (%) = 100 × $(PD_{solvent} - PD_{solution})/PD_{solvent}$

Where $PD_{solvent}$ and $PD_{solution}$ are the pressure differences in the solvent and solution, respectively, measured from a strip chart recording of pressures taken at two points, 12.7 cm apart, along a 1 mm pipe. Between sample runs, the rheometer was rinsed with tap water until the baseline returned to normal. Sample size was 100 ml and all measurements were made with water as the solvent. Sample observations were normalized (wt/ppm or mg/l) typically 100–500 wt/ppm. Our observations were reproducible to within 1–2%. We considered measurements that differed by less than 5% to be equivalent.

Our observations of drag reduction coefficients for wild type and mutant CPS (from 8 mutant strains) are summarized in Table 1. Mutant strains 1, 2 and 5 were spontaneous mutants, while strains 3, 4, 5, 6, and 8 were induced by nitrosoguanidine. All mutants showed a decrease in pyruvulation while altered NMR spectra have been detected only in the spontaneous mutants. Our results show a 10% improvement in drag reduction in the CPS from mutant bacteria. Furthermore, as also shown in Table 1, CPS from mutant bacteria is more resistant to mechanical shearing as determined by repeated observations of drag reduction with a rheometer.

TABLE 1

Characterization of K63 CPS Mutants: Drag Reduction Results

| STRAIN | % DRAG REDUCTION | % SHEAR STABILITY |
|---|---|---|
| K 63 wt | 55.9 | 84.9 |
| K63-JPL1 | 67.7 | 95.6 |
| K63-JPL2 | 66.7 | 95.6 |
| K63-JPL3 | 67.0 | 99.4 |
| K63-JPL4 | 67.6 | 98.2 |
| K63-JPL5 | 67.0 | 99.4 |
| K63-JPL6 | 67.6 | 95.7 |
| K63-JPL8 | 67.2 | 99.7 |

While we have presented a number of embodiments of this invention by way of examples, it is apparent that our basic construction can be altered to provide other embodiments that also employ our invention. The scope of our invention is defined by the scope of the claims, rather than by the examples, which are only intended to be illustrative.

We claim:

1. A method for producing an isolated capsular polysaccharide comprising the steps of:
   (a) providing a wild type bacterial strain that produces a capsular polysaccharide and a bacteriophage that degrades at least one capsular polysaccharide produced by the wild type bacterial strain;
   (b) selecting phage resistant mutants of the bacterial strain that produce a capsular polysaccharide;
   (c) propagating the mutants to obtain a culture thereof; and;
   (d) harvesting the altering capsular polysaccharides of the mutants.

2. The method for producing an isolated capsular polysaccharide of claim 1, wherein the wild type bacterial strain is *Klebsiella pneumoniae* 5845/82.

3. The method for producing an isolated capsular polysaccharide of claim 1 wherein the capsular polysaccharide is K63.

4. The method for producing an isolated capsular polysaccharide of claim 1 wherein the bacteriophage is phage K63.

5. The method for producing an isolated capsular polysaccharide of claim 1 wherein the step of selecting mutants comprises the step of treating the selected wild type bacterial strain with a mutagenic agent.

6. The method for producing an isolated capsular polysaccharide of claim 5 wherein the mutagenic agent is radiation of nitrosoguanidine.

7. The method for producing an isolated capsular polysaccharide of claim 1 wherein the step of selecting phage resistant mutants further comprises the steps of:
   (a) exposing bacterial cultures to degradative phage enzymes with substrate specificity for the capsular polysaccharide of the wild type bacterial strain; and
   (b) selecting those cultures surviving step (a) above that produce a capsular polysaccharide.

8. The method for producing an isolated capsular polysaccharide of claim 1 wherein the step of harvesting further comprises the steps of:
   (a) treating the mutant bacterial cultures with phage enzyme;
   (b) separating the capsular polysaccharide from other components of the treated mutant bacteria by centrifugation; and
   (c) precipitation of the supernatant obtained in step (b) above with cold isopropanol or cold ethanol.

9. The method for producing an isolated capsular polysaccharide of claim 8 wherein the step of separating further comprises the step of digestion of the precipitate with concentrated phage enzyme.

* * * * *